(12) United States Patent
Zhou

(10) Patent No.: US 8,368,264 B2
(45) Date of Patent: Feb. 5, 2013

(54) ELECTRIC CUTTING TOOL

(75) Inventor: Ximing Zhou, Beijing (CN)

(73) Assignee: Beijing Montagne Medical Device Co. Ltd, Beijing (CN)

( * ) Notice: Subject to any disclaimer, the term of this patent is extended or adjusted under 35 U.S.C. 154(b) by 363 days.

(21) Appl. No.: 12/665,757

(22) PCT Filed: Jun. 20, 2007

(86) PCT No.: PCT/CN2007/001936
§ 371 (c)(1),
(2), (4) Date: Aug. 12, 2010

(87) PCT Pub. No.: WO2008/154773
PCT Pub. Date: Dec. 24, 2008

(65) Prior Publication Data
US 2011/0018372 A1    Jan. 27, 2011

(51) Int. Cl.
*H02K 5/22* (2006.01)
(52) U.S. Cl. .............................. 310/50; 310/71; 310/47
(58) Field of Classification Search .............. 310/50, 310/47, 71, 89
See application file for complete search history.

(56) References Cited

U.S. PATENT DOCUMENTS

| 3,502,915 | A | * | 3/1970 | Moret et al. | .................... 310/47 |
| 4,728,876 | A |   | 3/1988 | Mongeon | |
| 6,059,806 | A |   | 5/2000 | Hoegerle | |
| 6,376,942 | B1 | * | 4/2002 | Burger et al. | ................... 310/47 |
| 6,683,396 | B2 | * | 1/2004 | Ishida et al. | .................... 310/50 |
| 2008/0191563 | A1 | * | 8/2008 | Meldert | ........................ 310/50 |

FOREIGN PATENT DOCUMENTS

| CN | 87215276 U | 8/1988 |
| CN | 2702706 Y | 6/2005 |
| CN | 2873105 Y | 2/2007 |

\* cited by examiner

*Primary Examiner* — Dang Le
(74) *Attorney, Agent, or Firm* — AKC Patents LLC; Aliki K. Collins

(57) ABSTRACT

An electric cutting tool including a housing (1) and a motor (2). The motor (2) is removably mounted in a cavity arranged at the back end of the housing (2), and the outer diameter of the motor (2) is matched with the diameter of the cavity. A turnover opening back cover (3) is hinged at the opening at the back end of the cavity. The back cover (3) is locked with the housing (1) by means of a locking structure arranged on its side, and presses against the back end of the motor (2) after closing. A pair of electrode posts (21) are provided at the front end of the motor (2), and a pair of electrode sockets (18) corresponding one-to-one with the pair of electrode posts (21) are provided in the bottom surface of the cavity. A circumferential stop structure is provided between the radial outer surface of the motor (2) and the inner wall of the cavity. The motor (2) is circumferentially fastened by the circumferential stop structure, causing the polarities of the electrode posts (21) and those of the electrode sockets (18) matching.

8 Claims, 2 Drawing Sheets

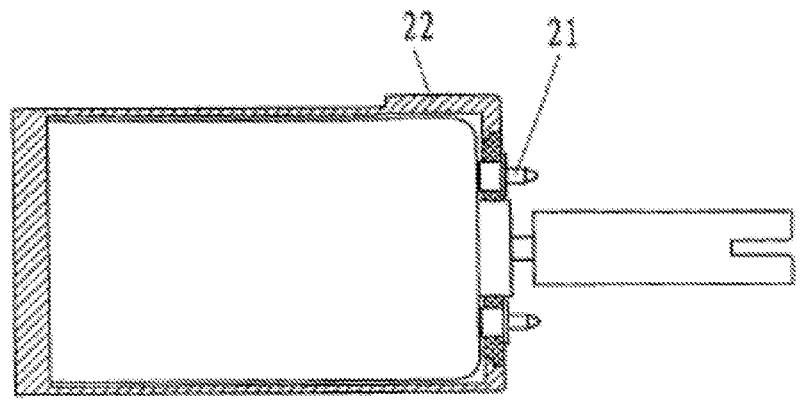
*FIG. 4*
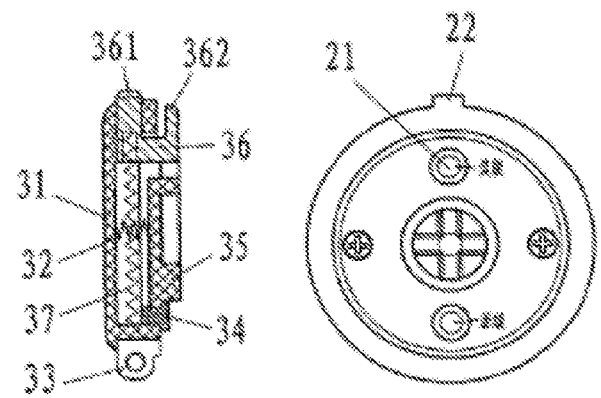
*FIG. 5*  *FIG. 3*
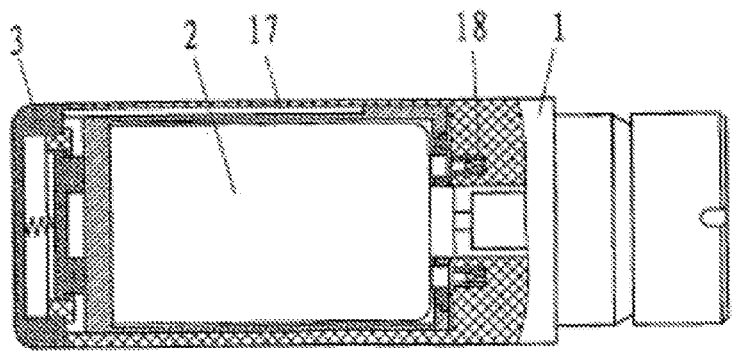
*FIG. 2*

ELECTRIC CUTTING TOOL

FIELD OF THE INVENTION

The present invention relates to an electric cutting tool, belonging to the field of medical appliances.

BACKGROUND

Previously, aiming at the problem of the prior electric cutting tool with an irremovable motor, the applicant had provided a combined operation power gun with a changeable motor and obtained the Chinese patent with the patent number being 200520144724.X. In the patent, electric connection of the motor is realized by the means that two ring-shaped electrodes arranged on the end part of the motor are respectively in contact with two needle-shaped electrodes arranged on a housing, The configuration can avoid misconnection for the electrodes without affecting the connection between the electrodes at any angle that the motor turns relative to the housing, however, because the electrode rings on the motor can not be designed wide enough and the needle-shaped electrodes on the housing can not be designed thick enough, the motor must be accurately located in the housing in order to ensure good contact between the electrodes, otherwise the contact area of the two electrodes may be changed thereby affecting electric conduction effect. In the patent, in order to prevent the motor from being freely rotated in the housing, a location lockgroove is arranged on the housing, a corresponding locating lug boss is arranged on the motor, and the motor is circumferentially fixed relative to the housing by matching the lug boss with the lock groove. Because the lock groove is arranged at the bottom of the cavity of the housing, the motor needs to be turned after being installed to align the lug boss to the lock groove, while only a little of the back end of the motor is exposed, therefore, the location mode causes some inconvenience to the assembly of the motor. Further more, in the specific embodiment of the specification, the patent describes a specific structure of a back cover, wherein the back cover is locked in the lock groove arranged on the housing by the lug boss arranged thereon; because the lug boss in the specific structure is a fixed structure, the locking assembly between the lug boss and the lock groove is getting more and more loose after being opened and closed at several times thereby finally affecting the reliable close of the back cover.

SUMMARY

Aiming at the defects of the prior patent, the present patent application aims at providing an electric cutting tool with different electrode connection mode and motor location mode. In order to achieve the purpose, the present patent application has the following technical scheme:

An electric cutting tool comprises a housing and a motor, wherein the motor is installed in an cavity arranged at the back end of the housing in a detachable way, and the outer diameter of the motor is matched with the diameter of the cavity; a turnover opening back cover is hinged at the opening at the back end of the cavity; the back cover is fixedly locked with the housing by means of a locking structure arranged on one side thereof, and presses against the back end of the motor after closing; a pair of electrode posts are arranged at the front end of the motor, and a pair of electrode sockets in one-to-one correspondence with the pair of electrode posts are arranged in the bottom surface of the cavity; a circumferential stop structure is arranged between the radial outer surface of the motor and the inner wall of the cavity; and the motor is circumferentially fixed by the circumferential stop structure, matching the polarities of the electrode posts with those of the electrode sockets.

Further, the electrode posts are banana electrodes.
Further, the electrode posts are needle-shaped electrodes.
Further, the circumferential stop structure consists of key grooves and keys which are mutually matched and arranged on the motor or on the inner wall of the cavity.
Further, the key groove is arranged on the radial outer surface of the motor; and the key is a key-shaped lug boss which is directly integrally formed on the inner wall of the cavity.
Further, the key groove is arranged on the inner wall of the cavity; and the key is a key-shaped lug boss which is directly integrally formed on the housing of the motor.
Further, the key-shaped lug boss is arranged on the outer surface of the motor near the front end thereof or on the outer surface of the motor near the back end thereof.
Further, the back cover comprises a back cover body, an overhead ring and a manual lock head; one radial side of the back cover body is provided with an axle hole for hinging the housing; the overhead ring is locked in the back cover body and can move along a fore-and-aft direction relative to the back cover body; a pressure spring for forwards pushing the overhead ring is arranged between the back end of the overhead ring and the back cover body; the manual lock head is locked on the other side of the back cover body opposite to the said axle hole and is provided with an operation surface and a lock platform, wherein the lock platform is used for being locked with the lock groove arranged on the housing and can be radially withdrawn inwards the back cover body once the operation surface is pressed; and the back cover body is internally provided with a return pressure spring of the manual lock head.

By adopting a novel electrode structure and using the key groove to circumferentially stop the motor, the present patent application does not only improve the reliability of electrode connection, but also facilitates the installation of the motor and can prevent the electrodes polarities from being connected by mistake. Further more, the manual lock head is arranged on the back cover, so that the back cover is convenient to close and open, thereby extending the service life of the back cover.

BRIEF DESCRIPTION OF THE DRAWINGS

FIG. 2 is an A-A cutaway view illustrated in FIG. 1;
FIG. 3 is an end view of the motor;
FIG. 4 is a cutaway view of the motor;
FIG. 5 is a structure schematic view of the back cover.

DETAILED DESCRIPTION OF THE INVENTION

Figure 1:
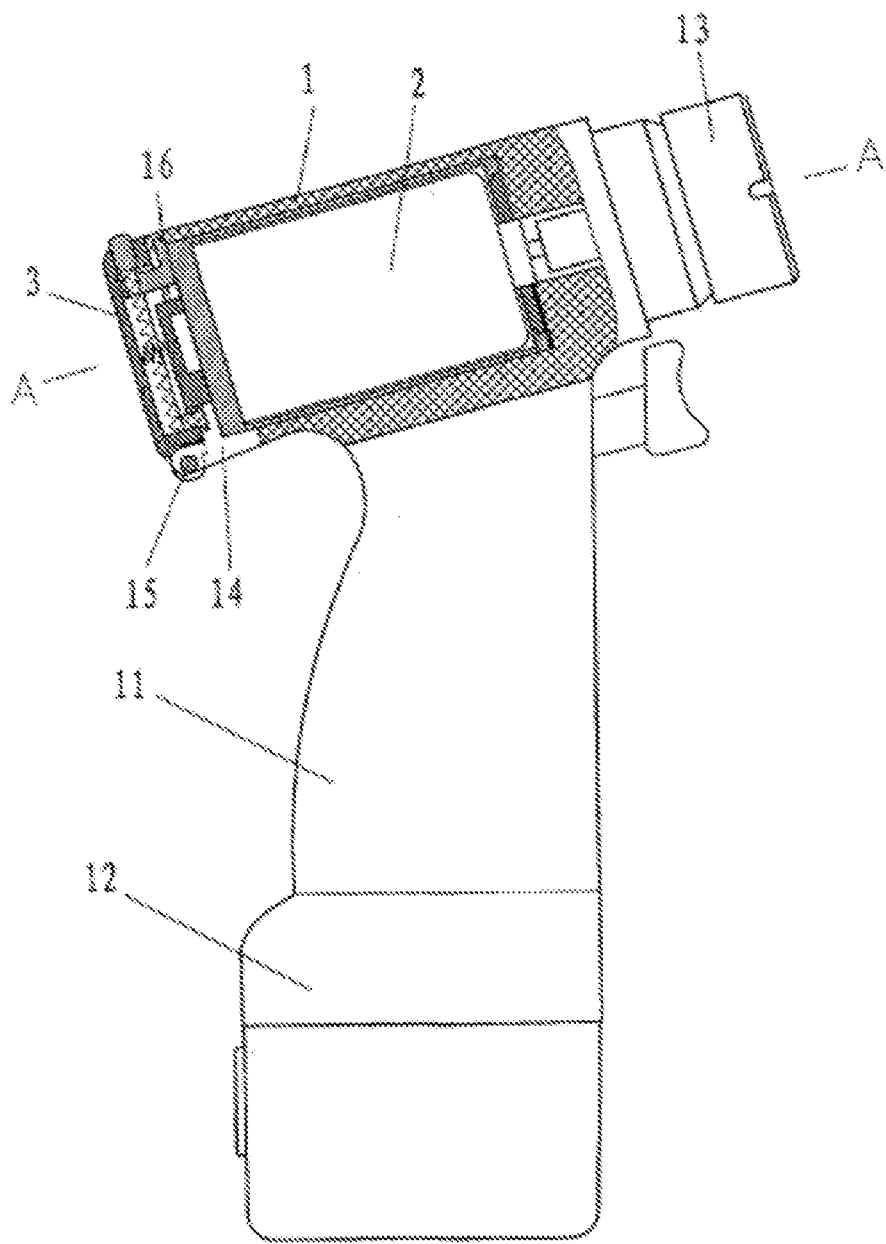
FIG. 1 is a cutaway view of the electric cutting tool.

In the FIG. 1 and the FIG. 2, the electric cutting tool of the present patent application comprises a housing 1 and a motor 2, wherein the housing 1 is provided with a handle 11, a battery 12 is accepted in the lower end of the handle, the front end of the housing 1 is provided with an installing seat 13 of a cutting head (not illustrated in the figures); in the FIG. 3 and the FIG. 4, the motor 2 is detachably arranged in an cavity arranged at the back end of the housing 1, the outer diameter of the motor 2 is matched with the diameter of the cavity, a pair of electrode posts 21 are arranged at the front end of the motor 2, a pair of electrode sockets 18 in one-to-one correspondence with the pair of electrode posts 21 are arranged in the bottom surface of the cavity of the housing 1, a key-shaped lug boss 22 is arranged on the outer surface of the motor 2 near the front end thereof, a key groove 17 penetrating through the whole axial length of the cavity is arranged on the inner wall of the cavity of the housing 1, through the key-shaped lug boss 22 being matched with the key groove 17, the motor 2 arranged in the cavity of the housing 1 is circumstantially fixed relative to the housing 1, meanwhile, the polarities of the electrode posts 21 on the motor 2 are matched with those of the electrode sockets 18 on the bottom face of the cavity of the housing 1; an opening at back end of the cavity of the housing 1 is provided with a back cover 3, in the FIG. 5, the back cover 3 comprises a back cover body 31, an overhead ring 35 and a manual lock head 36, wherein the lower edge of the back cover body 31 is provided with a hinged joint 33, the overhead ring 35 is locked in the back cover body 31 by a lock ring 34, a pressure spring 32 is arranged between the back end of the overhead ring 35 and the back cover body 31, the overhead ring 35 can move forwards and backwards relative to the back cover body 31, the manual lock head 36 is locked at the upper edge of the back cover body 31, the manual lock head 36 is provided with an operation surface 361 and a lock platform 362, wherein the lock platform 362 is used for locking a lock groove 16 arranged on the housing 1, the manual lock head 36 can be radially inwards withdrawn with the lock platform 362 arranged thereon towards the back cover body once the operation surface 361 is pressed down, a return spring 37 is arranged below the manual lock head 36, the lower end of the pressure spring supports against the back cover body 31 and the upper end of the pressure spring supports against a hole arranged on the manual lock head 36.

When being installed, the motor 2 is inserted into the cavity of the housing 1, after the back cover 3 is upwards overturned and closed, the overhead ring 35 on the back cover 3 always supports against the back end of the motor 2 under the effect of the pressure spring 32, so as to guarantee the connection stability between the electrode posts 21 on the motor 2 and the electrode sockets 18 on the housing 1.

The present patent application uses the electrode posts and the electrode sockets to replace the original needle-shaped electrodes and the ring-shaped electrodes, so as to simplify the electrode structure and improve the reliability of electrode connection. By adopting a circumferential stop structure of the motor which consists of a key groove and a key, and particularly by arranging the key groove into the cavity of the housing, after the key is arranged on the outer surface of the motor near the front end thereof, the motor is circumferentially stopped once being inserted into the cavity of the housing at the beginning, wherein the circumferential position of the motor is constantly kept in the whole process of inserting, therefore, the motor needs not to be turned in the cavity of the housing to search the circumferential position thereof, so that the motor can be conveniently installed, meanwhile, the polarities of the electrode posts are corresponding to those of the electrode sockets once the motor is inserted at the beginning, and the electrode posts are aligned with the electrode sockets, so that circumferential misalignment between the needle-shaped electrodes and the ring-shaped electrodes is eliminated in installation and good contact between the electrodes is provided. After the manual lock head on the back cover is arranged, the prior problem of serious abrasion between the lock platform and the lock groove is solved and the service life of the device is improved.

In the embodiment, the electrode posts also adopt needle-shaped electrodes or banana electrodes or other proper press-adopting structure electrodes.

The key groove can also be arranged on the outer surface of the motor, the key is arranged in the cavity of the housing, and the key also can be formed by a pin bolt or a separately installed key.

Further more, the circumferential stop structure which consists of the key groove and the key can also be realized by the structures of other forms, such as a motor with a polygonal cross section and an cavity of a housing matched therewith, a motor with a partially circular cross section and an cavity of a housing matched therewith, etc.

The detailed description only describes one specific embodiment of the present patent application which is not limited thereby, and any improvement and/or deformation made by the skilled in the art under the spirit which is not separated from the present patent application belong(s) to the protection scope of the present invention.

The invention claimed is:

1. An electric cutting tool comprising a housing and a motor, wherein the motor is installed in an cavity arranged at the back end of the housing in a detachable way, and the outer diameter of the motor is matched with the diameter of the cavity; a turnover opening back cover is hinged at the opening at the back end of the cavity; the back cover is locked with the housing by means of a locking structure arranged on one side thereof, and presses against the back end of the motor after closing; the electric cutting tool is characterized in that a pair of electrode posts are arranged at the front end of the motor, and a pair of electrode sockets in one-to-one correspondence with the pair of electrode posts are arranged in the bottom surface of the cavity; a circumferential stop structure is arranged between the radial outer surface of the motor and the inner wall of the cavity; and the motor is circumferentially fixed by the circumferential stop structure, matching the polarities of the electrode posts with those of the electrode sockets.

2. The electric cutting tool of claim 1, wherein the electrode posts are banana electrodes.

3. The electric cutting tool of claim 1, wherein the electrode posts are needle-shaped electrodes.

4. The electric cutting tool of claim 1, wherein the circumferential stop structure is consists of a key groove arranged on the motor and a key arranged on the inner wall of the cavity; and the key groove and the key are mutually matched.

5. The electric cutting tool of claim 4, wherein the key groove is arranged on the radial outer surface of the motor; and the key is a key-shaped lug boss which is directly integrally formed on the inner wall of the cavity.

6. The electric cutting tool of claim 4, wherein the key groove is arranged on the inner wall of the cavity; and the key is a key-shaped lug boss which is directly integrally formed on the housing of the motor.

7. The electric cutting tool of claim 6, wherein the key-shaped lug boss is arranged on the outer surface of the motor near the front end thereof or on the outer surface of the motor near the back end thereof.

8. The electric cutting tool of claim 1, wherein the back cover comprises a back cover body, an overhead ring and a manual lock head; one radial side of the back cover body is provided with an axle hole for hinging the housing; the overhead ring is locked in the back cover body and can move along a fore-and-aft direction relative to the back cover body; a pressure spring for forwards pushing the overhead ring is arranged between the back end of the overhead ring and the back cover body; the manual lock head is locked on the other side of the back cover body opposite to the axle hole and is provided with an operation surface and a lock platform, wherein the lock platform is locked with the lock groove arranged on the housing and can be radially withdrawn inwards the back cover body once the operation surface is pressed; and the back cover body is internally provided with a return pressure spring of the manual lock head.

* * * * *

UNITED STATES PATENT AND TRADEMARK OFFICE
CERTIFICATE OF CORRECTION

PATENT NO. : 8,368,264 B2  Page 1 of 1
APPLICATION NO. : 12/665757
DATED : February 5, 2013
INVENTOR(S) : Ximing Zhou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this

First Day of September, 2015

Michelle K. Lee
*Director of the United States Patent and Trademark Office*